US009603683B2

(12) United States Patent
Dierkes et al.

(10) Patent No.: US 9,603,683 B2
(45) Date of Patent: Mar. 28, 2017

(54) METHOD FOR PRODUCING A DENTAL RESTORATION BY CAD CASTING

(75) Inventors: Stephan Dierkes, Bremen (DE); Severin Seifert, Bremen (DE); Roland Strietzel, Lilienthal (DE)

(73) Assignee: BEGO BREMER GOLDSCHLAGEREI WILH. HERBST GMBH & CO. KG, Bremen (DE)

(*) Notice: Subject to any disclaimer, the term of this patent is extended or adjusted under 35 U.S.C. 154(b) by 874 days.

(21) Appl. No.: 13/997,573

(22) PCT Filed: Dec. 23, 2011

(86) PCT No.: PCT/EP2011/073997
§ 371 (c)(1),
(2), (4) Date: Aug. 29, 2013

(87) PCT Pub. No.: WO2012/085285
PCT Pub. Date: Jun. 28, 2012

(65) Prior Publication Data
US 2014/0008826 A1    Jan. 9, 2014

(30) Foreign Application Priority Data

Dec. 23, 2010  (DE) .................... 10 2010 064 142

(51) Int. Cl.
| | | |
|---|---|---|
| *A61C 13/00* | (2006.01) | |
| *A61C 13/20* | (2006.01) | |
| *A61C 13/08* | (2006.01) | |
| *C04B 28/06* | (2006.01) | |
| *A61C 13/34* | (2006.01) | |
| *C04B 14/10* | (2006.01) | |
| *B29L 31/00* | (2006.01) | |
| *B29C 33/38* | (2006.01) | |
| *C04B 14/06* | (2006.01) | |
| *C04B 111/00* | (2006.01) | |
| *C04B 111/32* | (2006.01) | |

(52) U.S. Cl.
CPC ........ *A61C 13/0004* (2013.01); *A61C 13/081* (2013.01); *A61C 13/20* (2013.01); *C04B 28/06* (2013.01); *A61C 13/34* (2013.01); *B29C 33/3842* (2013.01); *B29C 33/3857* (2013.01); *B29L 2031/7536* (2013.01); *C04B 14/06* (2013.01); *C04B 14/062* (2013.01); *C04B 14/10* (2013.01); *C04B 2111/00836* (2013.01); *C04B 2111/00939* (2013.01); *C04B 2111/32* (2013.01)

(58) Field of Classification Search
CPC ... A61C 13/0004; A61C 13/081; A61C 13/20; A61C 13/34; C04B 28/06; C04B 14/06; C04B 14/062; C04B 14/10; C04B 2111/00836; C04B 2111/00939; B29L 2031/7536; B29C 33/3842; B29C 33/3857

USPC ...... 264/16, 17, 19, 219, 227; 106/692, 695; 433/213
See application file for complete search history.

(56) References Cited

U.S. PATENT DOCUMENTS

| | | | | |
|---|---|---|---|---|
| 2004/0238981 A1* | 12/2004 | Weiss | ........................ | A61C 5/10 264/16 |
| 2005/0103228 A1* | 5/2005 | Rabe | .................... | A61C 13/081 106/38.2 |
| 2006/0115795 A1* | 6/2006 | Marshall | .................. | A61C 5/10 433/218 |

FOREIGN PATENT DOCUMENTS

| | | |
|---|---|---|
| DE | 10223883 A1 | 12/2003 |
| DE | 10332802 A1 | 3/2004 |
| DE | 202005020953 U1 | 2/2007 |
| DE | 102005056565 A1 | 6/2007 |
| DE | 102008036661 A1 | 2/2010 |
| EP | 0916430 A1 | 5/1999 |

(Continued)

OTHER PUBLICATIONS

Sunnegardh-Gronberg, Karin, "Calcium Aluminate Cement as Dental Restorative. Mechanical Properties and Clinical Durability", Umea University, Sweden, 2004, pertinent pp. 1 and 21-22 attached herein. The full document is restricted and cannot be attached, however it can be found at https://www.diva-portal.org/smash/get/diva2:142894/FULLTEXT01.pdf.*

(Continued)

*Primary Examiner* — Alison L Hindenlang
*Assistant Examiner* — Lawrence D Hohenbrink, Jr.
(74) *Attorney, Agent, or Firm* — Duane Morris LLP; J. Rodman Steele, Jr.; Gregory M. Lefkowitz

(57) ABSTRACT

A method for producing a dental restoration (D) by CAD casting is described, said method comprising the steps of a) recording three-dimensional, digital data of the dentition or of a part of the dentition of a patient, b) creating a virtual dental restoration (VD) using the recorded three-dimensional, digital data, wherein the virtual dental restoration (VD) is expanded in relation to the dental restoration (D) to be produced, c) preparing a model (M) using the created virtual dental restoration, such that the model (M) is expanded in relation to the dental restoration (D) to be produced, d) embedding the model (M) in an embedding compound (EM), e) hardening the embedding compound (EM) and removing the model (M), such that a casting mold is obtained, f) filling the casting mold, preferably by pouring, with a casting material (GM) and cooling the casting material (GM), such that the dental restoration (D) is obtained, and optionally the further steps of g) working the dental restoration (D), and h) veneering the dental restoration (D).

A novel embedding compound (EM) is also described that has no expansion or at least is only a slight expansion on setting.

12 Claims, No Drawings

(56) References Cited

FOREIGN PATENT DOCUMENTS

| EP | 1043094 A1 | 10/2000 |
|----|------------|---------|
| EP | 2062665 B1 | 5/2009 |
| EP | 1661529 B1 | 10/2011 |
| WO | 2004/037215 | 5/2004 |
| WO | 2008/066891 | 6/2008 |

OTHER PUBLICATIONS

PCT International Search Report and Written Opinion, PCT/EP2011/073997, dated Sep. 25, 2012 (16 pages).

First Examination Report (corresponding German Patent Application No. 10 2010 064 142.1), dated Jun. 10, 2011 (5 pages).

* cited by examiner

METHOD FOR PRODUCING A DENTAL RESTORATION BY CAD CASTING

CROSS-REFERENCE TO RELATED APPLICATIONS

This application is a §371 national stage entry of International Application No. PCT/EP2011/073997, filed Dec. 23, 2011, which claims priority to German Patent Application No. 10 2010 064 142.1 filed Dec. 23, 2010, the entire contents of which are incorporated herein by reference.

BACKGROUND OF THE INVENTION

In conventional dentistry, when casting a dental restoration, in particular a model casting or crowns and bridges, a model is created using wax or a photo-curable plastic from a previously created positive model, representing the oral situation of the patient or a part thereof. The three-dimensional proportions of the wax or plastic model are therefore identical to those of the dental restoration to be created. The wax or plastic model is normally embedded with an embedding compound and burned away once the embedding compound has hardened, so that a casting mold is obtained. Then the desired casting material is cast into the casting mold produced, such that once the casting material has cooled the dental restoration is obtained.

New developments in dentistry use CAD/CAM technology. As a result the design of the wax or plastic modes is no longer based on a positive model, as described above, but takes place virtually. In order to obtain three-dimensional, digital data, normally to begin with either the dentition or a part of the dentition of the patient is scanned in the mouth of the patient or initially an impression is taken of the dentition or a part of the dentition of the patient, which is then scanned. On the basis of the data set obtained a wax or plastic model is then normally created by printing or stereolithography, in order to obtain a model which in terms of the physical proportions corresponds to the dental restoration to be produced, and which then (as a working model) according to the conventional method outlined above is surrounded with an embedding compound, in order that once the wax or plastic model has been removed (normally by burning off) a casting mold is obtained, which is cast with a casting material, in order to obtain the desired dental restoration. Such methods are described, inter alia, in the following publications: U.S. Pat. No. 7,463,942B2, U.S. Pat. No. 7,383,094B2, U.S. Pat. No. 669,134B2, U.S. Pat. No. 6,915,178B2, U.S. Pat. No. 6,957,118B2, DE 3003435A1, [Schweiger: "Rapid Prototyping—Technik der Zukunft?", Dental-labor, 7 (2004), p. 1109] and [Schweiger: "Rapid Prototyping-Neue Fertigungswege in der Zahntechnik und Zahnmedizin", DIGITAL_DENTAL.NEWS, 2 (2008), p. 36].

In the prior art it known in the production of cast parts for dentistry to use a refractory embedding compound, the expansion values of which compensate for the unavoidable contraction of the casting materials used (during cooling of the casting material after pouring into the casting mold).

After casting, as the hardened casting material cools, the cast parts become smaller due to the thermal expansion of the solid casting material, and possible changes in the crystalline structure. As a result of the contraction of the casting material during cooling of the hardened cast part, the original dimensions change and a so-called "solid shrinkage" takes place. In the context of the present invention the term "solid shrinkage" thus means the shrinkage that takes place at room temperature upon cooling after the hardening temperature of the casting material or the solidus temperature of a metal alloy used as a casting material has been reached. As a rule this differs according to the casting material. The amount of solid shrinkage of certain casting materials is normally given as a contraction dimension, according to the substance by the linear expansion coefficients $\alpha$ (also known as the linear coefficient of thermal expansion or thermal expansion).

In the prior art attempts are made to counter the contraction of the casting material, that is to say the solid shrinkage, by an expansion of the embedding compound that compensates (in part or in full) for the contraction. In order to control the expansion values of the embedding compound quartz or another modification of crystalline $SiO_2$ (e.g. cristobalite) is often added to this. The expansion characteristics of the embedding compound can further be controlled through the nature and concentration of the blending liquid used for blending the embedding compound, in particular by the nature and concentration of the silicon dioxide nanoparticles that it contains. The overall expansion of the embedding compound up until the casting mold resulting from the hardened embedding compound is normally made up of the setting expansion, i.e. the expansion of the embedding compound as it hardens, and possibly also the thermal expansion of the embedding compound, which as a rule occurs when an embedded wax or plastic model is burned out. The embedding compounds used are accordingly normally designed in such a way that through their setting expansion and possibly the thermal expansion they are able to compensate for the solid shrinkage of the casting material as it cools (generally to room temperature). So normally, depending on the casting material used, a suitable embedding compound and the associated blending liquid are selected.

However, such an approach also comes with disadvantages. Thus, as described above, in such compounds crystalline $SiO_2$ is often used, in order to achieve the required thermal expansion capacity. When quartz or other modifications of crystalline $SiO_2$ are used, however, there is a risk, in particular after many years of unprotected exposure in a dental laboratory, of silicosis or even lung cancer.

Furthermore, the setting expansion in particular of the embedding compound normally used is subject to major variations. And as a result this behaves differently (inter alia as a function of the type and quality of the binder used), in particular under differing conditions during mixing (e.g. with regard to the processing temperature, mixing time and speed). Here it is the case that the greater the amount of the maximum setting expansion of the embedding compound to be achieved, the higher the absolute variation.

A further disadvantage of such an approach is that for various casting materials with different fixed variations as a rule in each case different combinations of embedding compound and blending liquid must be selected. Thus when the casting material to be used is changed as a rule the embedding compound and/or blending liquid must be changed, which can considerably slow or adversely affect the working or production process.

In addition, for phosphate bonded embedding compounds in particular, it is not possible to produce dental restorations with differing indications in a single casting mold and at the same time have a good fit. Thus for example a "6×" telescope and an anterior tooth telescope must be embedded and cast separately from one another (with different blending liquid concentrations).

A further challenge in the production of tailor-made dental restorations is the result of distortions due to the uneven hardening of the casting material during cooling after pouring this into the casting mold. Thus for example thinner areas cool more quickly than thicker ones. In the prior art no standard procedure is described for avoiding such distortions during casting. Occasional attempts at solving this problem are for example referred to by the term "core embedding". A disadvantage of this method, however, is that two different embedding compounds are required and have to be mixed. Furthermore, the production process is slowed by the fact that the second embedding compound can only be added once the first embedding compound has hardened or set.

As a result of all this the need arises for an improved method for producing tailor-made dental restorations, preferably by CAD casting, wherein the abovementioned disadvantages can be avoided or at least reduced.

BRIEF SUMMARY OF THE INVENTION

The present invention concerns a novel method for producing a dental restoration (D) by CAD casting, that is to say using a method in which on the basis of a CAD model an embeddable model is produced, which is then embedded with an embedding compound, so that once the model is removed from the hardened embedding compound a casting mold is obtained, which can be filled with the desired casting material or have this poured in, consisting of the following steps:
  a) recording three-dimensional, digital data of the dentition or of a part of the dentition of a patient,
  b) creating a virtual dentition restoration (VD) using the recorded three-dimensional, digital data, wherein the virtual dental restoration (VD) is expanded in relation to the dental restoration (D) to be produced,
  c) preparing a model (M) using the created virtual dental restoration, such that the model (M) is expanded in relation to the dental restoration (D) to be produced,
  d) embedding the model (M) in an embedding compound (EM),
  e) hardening the embedding compound (EM) and removing the model (M), such that a casting mold is obtained, filling the casting mold, preferably by pouring, with a casting material (GM) and cooling the casting material (GM) such that the dental restoration (D) is obtained, and optionally the further steps of
  g) working the dental restoration (D) and
  h) veneering the dental restoration (D).

The present invention further concerns a novel embedding compound (EM) for use in a method for producing a dental restoration (D) by CAD casting, preferably for use in a method according to the invention for producing a dental restoration (D), comprising or consisting of
  5 through 50, preferably 10 through 30 wt. % of calcium aluminate cement,
  40 through 95, preferably 70 through 90 wt. % of one or a plurality of refractory fillers and optionally
  0 through 5 wt. % of calcium sulfate and/or
  0 through 6 wt. % of one or a plurality of further additives,
wherein the embedding compound (EM) has a linear setting expansion of 0 through 0.75%, preferably of 0 through 0.3%, particularly preferably of 0 through 0.1% (for determination of the linear setting expansion, see below).

The present invention further concerns the use of an embedding compound (EM) according to the invention for producing a dental restoration (D) by CAD casting, preferably for producing a dental restoration (D) by a method according to the invention.

Further aspects of the present invention will be inferred from the following description, the examples and the attached claims.

Further aspects of the problem for the present invention can be inferred from the following description and in particular from the attached claims.

DETAILED DESCRIPTION OF THE INVENTION

The primary object for the present invention is achieved by a method for producing a dental restoration (D) by CAD casting, comprising the following steps
  a) recording three-dimensional, digital data of the dentition or of a part of the dentition of a patient;
  b) creating a virtual dental restoration (VD) using the recorded three-dimensional, digital data, wherein the virtual dental restoration (VD) is expanded in relation to the dental restoration (D) to be produced,
  c) preparing a model (M), preferably a wax or plastic model (M), using the created, virtual dental restoration, such that the model (M) is expanded in relation to the dental restoration (D) to be produced,
  d) embedding the model (M) in an embedding compound (EM),
  e) hardening the embedding compound (EM) and removing the model (M), such that a casting mold is obtained,
  f) filling the casting mold (for example by vacuum pressure casting or centrifugal casting), preferably by pouring, with a casting material (GM) and cooling the casting material (GM), such that the dental restoration (D) is obtained, and optionally the further steps of
  g) working the dental restoration (D) and
  h) veneering the dental restoration (D).

In CAD casting a CAD model (here a virtual dental restoration (VD)) is used to produce an embeddable model (here the model (M)), which is then embedded with an embedding compound, in order to obtain a casting mold following removal of the model from the hardened embedding compound, which can be filled or cast with the desired casting material.

The present invention preferably involves, for a dental restoration (D) framework for the dentures, in particular for crowns, bridges and prostheses or for accessory parts (e.g. attachments and bars).

The recording of the three-dimensional, digital data in step a) preferably takes place by a1) scanning the dentition or a part of the dentition in the mouth of the patient or a2) taking an impression of the dentition or a part of the dentition of the patient and subsequent scanning of the impression or a part of the impression. The scanning methods familiar to a person skilled in the art will be used here.

In step b), using the three-dimensional, digital data recorded in step a), a virtual dental restoration (VD) is created, which is expanded in relation to the dental restoration (D) to be produced. On the basis of this expanded, virtual dental restoration (VD) in step c) a model (M), preferably a wax or plastic model (M), is created, which is similarly expanded in relation to the dental restoration (D) to be produced, preferably to the same scale as the virtual dental restoration (VD). Accordingly, in terms of its proportions the model (M) preferably fully corresponds to the virtual, dental restoration (VD) created.

In the context of the present text, the expression "expanded in relation to the dental restoration (D) to be produced" means that the virtual dental restoration (VD) or the model (M) in relation to the dental restoration (D) to be produced either completely or at least in part, e.g. in one or a plurality of (selected) areas, is expanded. In this way advantageously both (in the context of a complete expansion) a solid shrinkage of the casting material (GM) occurring upon cooling of the casting material (GM) (see above) as a whole as well as (in the context of a possible additional, at least partial expansion in selected areas) any distortions, in particular as a result of areas of differing thickness of the dental restoration (D) to be created, can be compensated for completely or at least in part, so possible misfits can be avoided or at least reduced. Thin-walled areas or parts (such as clips for model casting or copings for bridges) in particular can according to the invention be advantageously provided with an additional expansion. In this way it is, in particular, advantageously possible, to produce large bridges with a more precise fit.

As described above, the unavoidable solid shrinkage of the casting material is normally, as described in the prior art, compensated for solely by the overall expansion of the embedding compound. Here the overall expansion of the muffle, e.g. the casting mold resulting from the embedding compound, with conventional embedding compound systems comprises the setting expansion and possibly a thermal expansion of the embedding compound (see above). The embedding compound and the type and concentration of the blending liquid are in particular selected as a function of the casting material used.

According to the present invention, however, advantageously any three-dimensional changes, which in particular are caused by the solid shrinkage of the casting material (GM) or any distortions, can be taken into account at the same time that the virtual dental restoration (VD) is created and when producing the model (M). In so doing the overall expansion of the embedding compound (EM) used can also advantageously be taken into account. Thus in the context of the method according to the invention any embedding compounds (EM), blending liquids and casting materials (GM) can be combined. It is self-evident to a person skilled in the art that when making the selection, it should preferably be ensured, however, that the overall expansion of the embedding compound (EM) is less than the amount of the (expected) solid shrinkage of the casting material (GM).

The (expected) solid shrinkage or the contraction of a casting material (GM) can be determined to a sufficient approximation from the linear coefficients of thermal expansion of the casting material (GM) by extrapolation (as far as the hardening or solidus temperature). The linear coefficient of thermal expansion is preferably determined using a dilatometer (e.g. by means of a DIL 801 from Bähr) by taking measurements in the range from room temperature to preferably a temperature of 600° C.

In the following, examples are given of the normal ranges of solid shrinkages or normal contraction of selected casting materials suitable for dental purposes (in each case in respect of the relative variation in length):
  base metal alloys or casting materials: e.g. CoCr alloys (solid shrinkage in the range of approximately 2.0% through approximately 2.6%), NiCr alloys (solid shrinkage in the range of approximately 1.8% through approximately 2.3%), titanium (solid shrinkage in the range of approximately 1.5% through approximately 1.6%);
  noble metals, or alloys thereof: e.g. high-gold alloys or palladium-based alloys (solid shrinkage in the range of approximately 1.3% through approximately 2%);
  silver-based alloys: solid shrinkage in the range of approximately 1.7% through approximately 2.1%.

Since the compensation of the solid shrinkage of the casting material (GM) used is achieved according to the invention completely or at least in part by the expansion of the virtual dental restoration (VD) and of the model (M) (as described above) and no, or no complete, compensation through the expansion of the expansion compound used has to take place, the method according to the invention allows the production of dental restorations from various casting materials (GM), wherein a particular embedding compound and an associated blending liquid can be worked with continuously.

Particular preference is for a method according to the invention (as described above), wherein the virtual dental restoration (VD) and/or the model (M) is expanded in relation to the dental restoration (D) to be produced overall by 0.025 through 3%, preferably by 1 through 2.5%, in relation to the relative change in length. This means that the (expansion) change relates to the length.

Any additional expansion in selected areas of the virtual dental restoration (VD) or of the model (M) according to a preferred embodiment of the present invention is in the range 0.025 through 1%, particularly preferably in the range 0.05 through 0.2%, wherein the (expansion) change relates to the length, i.e. relates to the relative change in length.

Accordingly, particular preference is for a method according to the invention (as described above), wherein the virtual dental restoration (VD) and/or the model (M) in relation to the dental restoration (D) to be produced are not uniformly expanded. Thin-walled areas or parts, in particular (for example clips for model casting or copings for bridges) according to the invention can advantageously be provided with another or an additional expansion in relation to other areas or parts. Accordingly, a method according to the invention (as described above) is particularly preferred, wherein one or a plurality of areas of the virtual dental restoration (VD) and/or of the model (M) in relation to the dental restoration (D) to be produced (compared to the other areas) are further expanded, wherein this further expansion in one or a plurality of selected areas of the virtual dental restoration (VD) or of the model (M) is preferably in the range 0.025 through 1%, particularly preferably in the range 0.05 through 0.2%, wherein the (expansion) change relates to the length, i.e. is in relation to the relative change in length.

In the context of the method according to the invention in particular the choice of embedding compound (EM), associated blending liquid and casting material (GM) to be used in the creation of the virtual dental restoration (VD) according to step b) must be taken into consideration.

In the context of the method according to the invention advantageously any expected distortions (as described above) can be taken into consideration, wherein one or a plurality of areas of the virtual dental restoration (VD) and of the model (M) are expanded in relation to the dental restoration (D) to be produced such that any distortions occurring during the further production process are at least partially or preferable completely compensated for.

When creating the virtual dental restoration (VD) in the context of the method according to the invention, therefore, apart from the embedding compound (EM), the associated blending liquid and the casting material (GM) to be used other factors, e.g. areas with different thickness or differently designed elements and their arrangement in the dental restoration (D) to be produced or the size of the dental restoration (D) to be produced, are preferably taken into consideration.

Furthermore, in the context of a method according to the invention advantageously the size and/or speed of cooling of the casting mold and of the casting material (GM) can be taken into consideration. As a rule the cooling of the casting mold and the cooling or hardening of the casting material (GM) actually takes place in the air at room temperature. But it is sometimes advantageous to increase the speed of cooling, for example by using a (cooled) water bath. More rapid cooling can have a positive effect on the microstructure of the dental restoration (D). So, for example, dental restorations (D) can be obtained which have improved strength and/or elongation at fracture. In addition, more rapid cooling accelerates the production process overall. However, a higher speed of cooling means that the temperature gradient within the casting material (GM) (from the outside in) is increased, such that there is a danger of the casting material (GM) hardening unevenly, which in turn can result in distortions and thus associated misfits. The method provided by the invention, however, advantageously allows such misfits to be reduced or even eliminated, in that when the virtual dental restoration (VD) is created an expected distortion, which can be determined empirically, is taken into consideration (for the empirical determination of such distortions see also: Egner-Walter, "Vorhersage des Verzugs dünnwandiger Druckgußteile" (*Predicting the distortion of thin-walled cast parts*), Giesserei 93, 12 (2006), p. 26). Accordingly, a method according to the invention is more suitable than a conventional method, in particular for CAD casting where the speed of cooling has to be increased.

In summary, when creating the virtual dental restoration (VD) in the context of the method according to the invention preferably a number of factors, as described above, are preferably taken into consideration, in order to determine the degree of the expansion (and possible (furthers) expansions for selected areas) in respect of the dental restoration (D) to be produced. To this end a program is preferably used, which automatically or through user input captures the various factors to be taken into consideration. On the basis of these captured factors one or a plurality of different scaling factors (in relation to the dental restoration to be produced (D)) can then be assigned automatically or by the user to the virtual dental restoration (VD).

In particular in step b) of the method according to the invention when creating the virtual dental restoration (VD) initially, as a function of the expected solid shrinkage of the casting material (GM) and possibly the overall expansion of the embedding compound (EM), a uniform scaling factor is determined. Preferably then further, possibly different scaling factors for different areas or elements of the dental restoration are (empirically) determined, in order to compensate for any expected distortions. If necessary the various scaling factors are (empirically) determined here also as function of the position of the different areas or elements. Thus, for example, areas or elements in the anterior region to some extent require a smaller scaling factor than areas or elements in the lateral region of the mouth.

In connection with the method according to the invention it is therefore in particular preferred to take into consideration any differing geometries of the dental restoration to be produced when the virtual dental restoration (VD) is created and the model (M) is prepared. In order to ensure a better fit of the dental restoration to be produced, in the context of the method according to the invention initially (standard) models of standard parts with different geometries (e.g. for model casting (plate and brackets), for copings (molar and incisor) and for bridges (3, 6 and 9)), are in each case produced with different scaling factors. These (standard) models are then embedded and then burned out, in order to obtain corresponding casting molds. After pouring the desired casting material (GM) into the casting molds the various (standard) dental restorations are obtained. Through fit tests with the standard dental restoration particularly suitable scaling factors for determining the expansion to be set for the virtual dental restoration (VD) or the model (M) as a whole and for individual areas or elements can be determined.

The casting material (GM) for filling, preferably for pouring into, the casting mold in step f) is preferably selected from the group consisting of cobalt, nickel, chromium, titanium, gold, silver, palladium and alloys thereof.

The model (M) described in the present text (M) is advantageously suitable for embedding in an embedding compound (EM) and following hardening of the embedding compound (EM) removal therefrom, wherein the removal preferably takes place by burning out.

The model (M) is in particular a wax or plastic model (M). In the context of the present invention preferable methods used for producing models (M) are for example milling, stereolithography, laser sintering, laser fusion, 3D printing and fused deposition modeling (FDM), wherein the combustion residue of the modeling material is preferably less than 0.1% (see EN ISO 15854:2005 (D)). Particularly preferably the model (M) is a wax or plastic model (M), produced by means of the rapid prototyping (RP) method.

In the context of the present invention either a wax model (M) or also a plastic model (M) is particularly preferred. Wax models (M) frequently have a particularly advantageous dewaxing behavior, so that when the wax model (M) is removed by burning out at the most only low stresses occur in the casting mold, which in turn reduces the danger of streaking or cracking of the casting mold in particular when a large or voluminous dental restoration is to be produced. Plastic models (M) are on the other hand often preferred due to their greater ease of handling, since compared to wax models at high temperatures, in particular at temperatures of up to 60° C., they have little or no tendency to deform.

As described above, a method according to the invention optionally comprises the additional step g) or the additional steps g) and h). The working and possible veneering of the dental restoration (D) can be performed using methods familiar to the person skilled in the art.

With regard to the above statements a method according to the invention (as described above) is particularly preferred, wherein (i) the virtual dental restoration (VD) and/or
(ii) the model (M)
in relation to the dental restoration (D) to be produced is/are expanded such that the solid shrinkage of the casting material (GM) occurring when the casting material (GM) cools is/are partially or (at least almost) totally balanced out, i.e. compensated for.

To the extent that in the context of the method according to the invention an embedding compound (EM) is used, where an overall expansion, i.e. a setting expansion and possibly a thermal expansion, can be expected, to be taken into consideration in the context of the production of the dental restoration (D), which at least partly compensates for the solid shrinkage of the casting material (GM), the following preferably applies: The virtual dental restoration (VD) and the model (M) are expanded in relation to the dental restoration (D) to be produced such that the expected solid shrinkage upon cooling of the casting material (GM) in the framework is compensated for such that on the one hand the expansion (setting expansion) occurring when the embedding compound (EM) hardens and any thermal expansion of embedding compound (EM) (e.g. when the model (M)) is burned out) and the expansion selected for the virtual dental restoration (VD) and on the other hand the solid shrinkage occurring when the casting material (GM) cools is completely or at least almost completely eliminated. Here preferably an embedding compound (EM) must be used, the overall expansion of which is lower than the amount of the solid shrinkage of the casting material (GM).

According to an aspect of the present invention, in the context of a method according to the invention it is particularly preferred if the virtual dental restoration (VD) and/or the model (M) is expanded in relation to the dental restoration to be produced such that as a result 25% or more, preferably 50% or more, particularly preferably 75% or more of the solid shrinkage of the casting material (GM) is balanced out (compensated for).

To the extent that in a method according to the invention (as described above) the solid shrinkage of the casting material (GM) is to be balanced out completely, or at least almost completely by the expansion selected in steps b) and c), according to the invention it is preferred to use an embedding compound (EM), having the lowest possible overall expansion, in particular the lowest possible setting expansion. Such an embedding compound offers the advantage that the scaling factor(s) to be selected in steps b) and c) primarily have to be selected as a function of the solid shrinkage of the casting material (GM), but not or at least hardly as a function of the embedding compound (EM) used. Such an embedding compound (EM) (according to the invention) is described in more detail in the following.

Accordingly, a further aspect of the present invention concerns a (hardenable) embedding compound (EM) for use in a process for producing a dental restoration (D) by CAD casting, preferably for use in a method according to the invention (as described above), comprising or consisting of 5 through 50, preferably 10 through 30 wt. % of a calcium aluminate cement, preferably a calcium aluminate cement according to DIN EN 14647,
40 through 95, preferably 70 through 90 wt. % of one or a plurality of refractory fillers and optionally
0 through 5 wt. % of calcium sulfate and/or
0 through 6 wt. % of one or a plurality of further additives,
wherein the embedding compound (EM) has a linear setting expansion of 0 through 0.75%, preferably of 0 through 0.3%, particularly preferably of 0 through 0.1%, i.e. wherein the embedding compound (EM) during the hardening (setting), in particular during the hardening in step e) of a method according to the invention (as described above), expands by 0 through 0.75%, preferably by 0 through 0.3%, particularly preferably by 0 through 0.1%, in relation to the relative change in length, i.e. wherein the (expansion) change relates to the length.

The "linear setting expansion" of an embedding compound (EM) must be determined in the context of the present invention with the setup according to Dreyer-Jörgensen. Here a vertical casting ring filled with (hardenable) embedding compound (EM) has its surface covered with a watch glass, the displacement of which, caused by the expansion of the embedding compound (EM) as it hardens, is measured with a dial gauge (for details see: K. D. Dreyer-Jörgensen, "*Study of the setting expansion of gypsum*", Acta Odontol Scand, 21, 227 (1973)).

Prior to the embedding of the model (M) a blending liquid, comprising water or preferably consisting of water, is preferably added to the embedding compound (EM), so that the embedding compound exists in the form of a flowable mortar. Here the ratio of the total quantity (in wt. %) of blending liquid, preferably of water, to the total quantity (in wt. %) of other ingredients of the embedding compound (EM) (see above) is preferably in the range 10:100 through 30:100, preferably in the range 15:100 through 20:100.

Dental embedding compounds known in the prior art, i.e. embedding compounds for producing a dental restoration normally consist of the bonding system of ammonium phosphate and magnesium oxide. Here these embedding compounds, as described by way of introduction, are normally selected such that through their overall expansion they are able to compensate for the solid shrinkage of the casting material.

On the other hand, in the context of the present invention, however, an embedding compound (EM) is preferred which has a particularly low overall expansion. Particular preference is for an embedding compound (EM) (as described above) for use in a method according to the invention (as described above), wherein the model (M) in step e) at a preheating temperature which is approximately 450° C. below the temperature selected for filling or pouring in step f), is removed by burning out, and wherein the embedding compound (EM) upon heating from room temperature to preheating temperature expands by 0 through 0.75%, preferably by 0 through 0.5%, preferably by 0 through 0.3%, particularly preferably by 0 through 0.1%, in relation to the relative change in length. The change in length, i.e. the relative (percentage) change in length of the embedding compound (EM) upon heating from room temperature to the preheating temperature must in the context of the present invention be determined by means of a dilatometer (e.g. DIL 801 from Bähr) (see above).

During the pouring of the casting mold with casting material (GM) that preferably takes place in step f) of a method according to the invention preferably as a function of the casting material (GM) used a (casting) temperature in one of the following ranges is selected:

1 300° C. through 1 600° C., in particular when using base-metal alloys as the casting material (GM) (e.g. CoCr alloys or NiCr alloys),
1 100° C. through 1 350° C., in particular when using high-gold alloys as casting material (GM),
1 325° C. through 1 500° C., in particular when using palladium-based alloys as the casting material (GM),
1 150° C. to 1 350° C., in particular when using silver-based alloys as the casting material (GM), and
1 750° C. through 1 850° C., in particular when using titanium as the casting material (GM).

The preheating temperature is in particular in the range 650 through 1 250° C., particularly preferably in the range 700 through 1 000° C. Where titanium is used as the casting material (GM), the preheating temperature is particularly preferably in the range 900 through 1250° C., wherein the thermal expansion is determined preferably at a temperature in the range of approximately 1 100° C.

The removal of the model (M) by burning out at the preheating temperature described above leads (due to the resultant preheating of the mold) advantageously to a particularly good casting result. For an ideal outcome the preheating temperature must be selected as a function of the casting material (GM) used.

Calcium aluminate cement is already widely used as a binder in the construction industry, both as a pure binder but also in mortar formulations. Calcium aluminate cement is known as a refractory binder and is mainly used for furnace linings and in high-grade construction chemical formulations. Similarly calcium aluminates are generally used in combination with calcium sulfate as ettringite-forming binder ingredients for dense mortars (as described for example in EP 1785405A2 and US2006/0118006A1). In the area of (dental) precision casting in accordance with the prior art calcium aluminate cement or calcium aluminates are already used as binders (see for example US2081558 and US2911311). Furthermore, dental fillers have already been proposed in combination with calcium aluminate cements as binders (see for example US4689080 and US6620232B1).

Above all for very high melting alloys (e.g. titanium and zirconium alloys) embedding compounds with calcium aluminates have already been described (see for example EP1461173B1 and EP1611977B1). In EP1461173B1, for example, an embedding compound with calcium aluminates is described, which according to claim 1 of EP1461173B1 is to be used for high melting casting materials. Such casting materials are stated in the description to be titanium and titanium alloys. According to EP1461173B1, however, unlike the present invention, the solid shrinkage of the casting material is not achieved by an (intentionally selected) expansion of a virtual dental restoration (VD) or of a model (M) (as described above) in relation to the dental restoration to be produced. Rather, according to EP1481173B1, and also as described by way of introduction in connection with the known prior art, a compensation of the solid shrinkage of the casting material is achieved through a (compensatory) expansion of the embedding compound. Here the necessary expansion of the embedding compound is controlled by the addition of selected ingredients. In this connection, by way of example the reaction of aluminum dioxide and magnesium oxide to form spinel at above 850° C. is mentioned, wherein the resulting (thermal) expansion of the embedding compound corresponds to the solid shrinkage of a titanium alloy (to be used according to EP1461173B1). In fact according to EP1461173B1 the solid shrinkage of the titanium alloy is less than that of conventional dental alloys (such as for example gold- or cobalt-chromium alloys), such that the embedding compounds described in EP1461173B1 tend to have a low (thermal) expansion. An embedding compound as described in connection with the present invention, in particular an embedding compound with a linear setting expansion as described above, is not described in EP1461173B1 however.

An embedding compound (EM) according to the invention (as described above) has a particularly low, preferably no, (linear) setting expansion. The use of such an embedding compound (EM) preferred according to the invention advantageously leads to the possibility of the scaling factors in step b) of a method according to the invention (as described above) being determined independently or at least almost independently of the overall expansion of the embedding compound (EM). In addition, the absence of or at all events low setting expansion, in a number of production processes with identically selected embedding compounds (EM), advantageously leads to lower absolute variations, so that more consistent casting results can be achieved.

With regard to the at all events low thermal expansion described above of an embedding compound (EM) preferred according to the invention, the proportion of crystalline $SiO_2$ in the embedding compound compared with conventional embedding compounds can be reduced. Particular preference is therefore for an embedding compound (EM) according to the invention, comprising less than 30 wt. %, preferably less than 10 wt. %, preferably less than 1 wt. % of crystalline $SiO_2$, particularly preferably wherein the embedding compound (EM) is free from crystalline $SiO_2$, in particular free from quartz and cristobalite. In this way the danger of silicosis and the risk of lung cancer are advantageously reduced or avoided.

A further advantage of the embedding compound (EM) according to the invention with an aluminous cement base is high storage stability, in particular compared with phosphate-bonded binder systems, in addition, the ingredients of an embedding compound (EM) according to the invention with regard to their composition and any impurities present advantageously have no strong variations, so that reproducible results can be achieved.

A particular advantage of the embedding compound (EM) according to the invention (as described above) is also that as the blending liquid for the embedding compound (EM) water, in particular distilled water, can be used, so that no special blending liquids are necessary, which could possibly adversely affect the production of a dental restoration.

Preference according to the invention is for an embedding compound (EM) (as described above), wherein the, or one, a plurality of or all of the refractory fillers is or are selected from the group consisting of clay, in particular tabular clay and reactive clay, spinel ($MgAl_2O_4$), mullite, mullite-zirconia, amorphous $SiO_2$, in particular fused silica, crystalline $SiO_2$, in particular quartz and other modifications of crystalline $SiO_2$ (e.g. cristobalite), and mineral fibers. Here the ingredients can each be contained in various grain size fractions.

Particularly preferably an embedding compound (EM) according to the invention comprises or consists of the following ingredients:
  5 through 50 wt. % of calcium aluminate cement,
  10 through 30 wt. % of amorphous $SiO_2$, in particular fused silica,
  10 through 70 wt. % of clay ($Al_2O_3$),
  0 through 40 wt. % of spinel,
  0 through 10 wt. % of mineral fibers,
  0 through 5 wt. % of calcium sulfate (alpha-hemihydrate, anhydrite),
  0 through 1 wt. % of setting accelerators and
  0 through 3 wt. % of dispersants.

A setting accelerator can be contained both in an embedding compound (as described above) and in a blending liquid (as described above). The setting accelerators used according to the invention are preferably water-soluble. For the setting accelerator a lithium salt is preferably used, particularly preferably lithium carbonate. Lithium carbonate can, directly as a powder or in the form of a coating of a powder ingredient, either be added to an embedding compound (EM) in the form of a dry mixture or dissolved in the blending liquid, in particular (deionized) water.

Where the embedding compound (EM) is in the form of a dry mixture and does not contain any setting accelerator, according to the invention it is preferred to use a blending liquid which comprises a setting accelerator. Here the proportion of setting accelerator, in relation to the total weight of the blending liquid, is preferably 0.01 through 0.1 wt. %, preferably 0.03 through 0.08 wt. %. The setting accelerator is particularly preferably lithium carbonate.

According to the invention dispersive clay is preferred as the dispersant, that is to say clay which has a coating or an addition of both a dispersant and preferably also a setting accelerator (e.g. lithium carbonate).

In the context of the present invention the setting of the binder system described above consisting of embedding compound and blending liquid preferably takes place hydraulically.

An embedding compound (EM) according to the invention (as described above), in particular a embedding compound (EM) according to the invention referred to as preferred is particularly well-suited for use in a method according to the invention (as described above).

Accordingly, the present invention according to a further, particularly preferred aspect, concerns a method according to the invention for producing a dental restoration (D) by CAD casting (as described above), wherein the embedding compound (EM) for embedding of the model (M) in step d) is an embedding compound according to the invention (as described above). For preferred embodiments of the method that stated above applies by analogy.

A further aspect of the present invention concerns the use of an embedding compound (EM) according to the invention (as described above) for producing a dental restoration (D) by CAD casting, preferably for producing this according to a method according to the invention (as described above). Here, for preferred embodiments of the embedding compound (EM) and of the method for producing the dental restoration (D) that stated above applies by analogy.

In the following the present invention is described in more detail by using an example. The example selected represents merely a preferred embodiment of the present invention, however. Further aspects and preferred embodiments of the present invention are described above.

Production of an embedding compound ('EM) according to the invention and use thereof in a method for producing a dental restoration (D):

The following ingredients were used for producing an embedding compound (EM) according to the invention:

| Ingredient | Description | Proportion [wt. %] |
|---|---|---|
| Calcium aluminate cement | CA-270 (Almatis) | 29.985 |
| Fused silica | TECO-SIL 50/100 (Quarzwerke) | 15.0 |
| Clay (Al$_2$O$_3$) | T60; 0-0.3 mm (Almatis) | 10.0 |
| Clay (Al$_2$O$_3$) | T60; −45 μm LI (Almatis) | 5.0 |
| Clay (Al$_2$O$_3$) | E-SY 1000 (Almatis) | 25.0 |
| Spinel | AR78; −45 μm (Almatis) | 6.5 |
| Spinel | AR78; −90 μm (Almatis) | 7.0 |
| Dispersive clay (Al$_2$O$_3$) | ADW 1 (Almatis) | 1.5 |
| Accelerator (Li$_2$CO$_3$) | <100 μm (Chemetall) | 0.015 |

The individual ingredients were homogenously mixed using a mixer (60 s in the EasyMix from BEGO). For mixing the embedding compound distilled water was added to the dry mixture (17 ml liquid per 100 g dry mixture) and then mixed for 60 s with a stirring device (EasyMix from BEGO).

With the resulting flowable mortar, e.g. the embedding compound (EM) now also containing a blending liquid (here: water), a wax model (M), namely a 3-way wax bridge, was embedded and placed for 15 minutes in the vacuum cabinet. After 20 to 30 minutes the hardened casting mold (muffle) was removed and placed in the preheating furnace at 1 000° C. After 1 hour a casting material (GM) (here: Wirobond 280 alloy from BEGO) was cast into the preheated casting mold. Once the casting mold had completely cooled to room temperature the dental restoration was removed.

The invention claimed is:

1. A method for producing a dental restoration (D) by CAD casting, comprising:
   a) recording three-dimensional, digital data of a dentition or of a part of a dentition of a patient;
   b) creating a virtual dental restoration (VD) using the recorded three-dimensional, digital data;
   c) selecting an embedding compound to be used to create a model (M) from the virtual dental restoration (VD);
   d) determining a linear setting expansion factor of the selected embedding compound;
   e) selecting a casting material (GM) to be used to create the dental restoration (D) from the model (M);
   f) determining a coefficient of thermal expansion of the selected casting material;
   g) virtually expanding the virtual dental restoration (VD) relative to the recorded dentition data based on the determined linear setting expansion factor and the determined coefficient of thermal expansion;
   h) preparing the model (M) using the virtually expanded virtual dental restoration;
   i) embedding the model (M) in the selected embedding compound (EM);
   j) hardening the embedding compound (EM) and removing the model (M), so that a casting mold is obtained;
   k) filling the casting mold with the selected casting material (GM) and cooling the casting material (GM) such that the dental restoration (D) is obtained.

2. The method as claimed in claim 1, wherein the three-dimensional, digital data in step a) is recorded by
   a1) scanning the dentition or a part of the dentition in the mouth of the patient or
   a2) taking an impression of the dentition or a part of the dentition of the patient and then scanning the impression or a part of the impression.

3. The method as claimed in claim 1, wherein the casting material (GM) for filling the casting mold is selected from the group consisting of cobalt, nickel, chromium, titanium, gold, silver, palladium and alloys thereof.

4. The method as claimed in claim 1, wherein the model (M) is a wax or plastic model (M).

5. The method as claimed in claim 1, wherein
   (i) the virtual dental restoration (VD) and/or
   (ii) the model (M)
   in relation to the dental restoration (D) to be produced is or are expanded such that the solid shrinkage of the casting material (GM) which takes place when the casting material (GM) cools is or are partly or completely compensated for.

6. The method of claim 1, wherein the embedding compound (EM) comprises
   5 through 50 wt. % of calcium aluminate cement,
   40 through 95 wt. % of one or a plurality of refractory fillers, and optionally
   0 through 5 wt. % of calcium sulfate and/or
   0 through 6 wt. % of one or a plurality of further additives; and
   wherein the model (M) is removed by burning out, and wherein the embedding compound (EM) upon heating from room temperature to a preheating temperature expands by 0 through 0.75% in relation to the relative change in length.

7. The method as claimed in claim 1, wherein the embedding compound (EM) for the embedding of the model (M) in step i) is an embedding compound comprising:
   5 through 50 wt. % of calcium aluminate cement,
   40 through 95 wt. % of one or a plurality of refractory fillers, and optionally
   0 through 5 wt. % of calcium sulfate and/or
   0 through 6 wt. % of one or a plurality of further additives,
   wherein the embedding compound (EM) has a linear setting expansion of 0 through 0.75%.

8. The method as claimed in claim 1, wherein the embedding compound (EM) for the embedding of the model (M) in step i) is an embedding compound comprising:
   5 through 50 wt. % of calcium aluminate cement,
   70 through 95 wt. % of one or a plurality of refractory fillers, and optionally
   0 through 5 wt. % of calcium sulfate and/or
   0 through 6 wt. % of one or a plurality of further additives,
   wherein the embedding compound (EM) has a linear setting expansion of 0 through 0.75%.

9. The method of claim 1, wherein the embedding compound (EM) comprises
   5 through 50 wt. % of calcium aluminate cement,
   70 through 95 wt. % of one or a plurality of refractory fillers, and optionally
   0 through 5 wt. % of calcium sulfate and/or
   0 through 6 wt. % of one or a plurality of further additives; and
   wherein the model (M) is removed by burning out, and wherein the embedding compound (EM) upon heating from room temperature to a preheating temperature expands by 0 through 0.75% in relation to the relative change in length.

10. An embedding compound (EM) for use in a method for producing a dental restoration (D) by CAD casting, comprising:
    5 through 50 wt. % of calcium aluminate cement;
    70 through 95 wt. % of one or a plurality of refractory fillers;
    0 through 5 wt. % of calcium sulfate; and
    0 through 6 wt. % of one or a plurality of further additives; and
    wherein the embedding compound (EM) has a linear setting expansion of 0 through 0.75%.

11. The embedding compound (EM) as claimed in claim 10, wherein the embedding compound (EM) comprises less than 30 wt. % of crystalline $SiO_2$.

12. The embedding compound (EM) as claimed in claim 10, wherein one or more of the refractory fillers are selected from the group consisting of clay, spinel, amorphous $SiO_2$.

* * * * *